United States Patent [19]

Tomidokoro et al.

[11] 4,180,468
[45] Dec. 25, 1979

[54] DISUBSTITUTED ALIPHATIC CARBOXYLAMIDOAMINES AS WELL AS DETERGENTS AND TOILETRY COMPOSITIONS CONTAINING SAME

[75] Inventors: Susumu Tomidokoro, Funabashi; Toshiyuki Ukigai, Yachiyo; Toshio Takahashi, Narashino; Daini Saika, Chiba, all of Japan

[73] Assignee: The Lion Fat & Oil Co., Ltd., Tokyo, Japan

[21] Appl. No.: 855,056

[22] Filed: Nov. 25, 1977

[30] Foreign Application Priority Data

Dec. 1, 1976 [JP] Japan .................. 51/144356

[51] Int. Cl.² .......................... C09F 5/00; C11D 9/30; A61K 7/06
[52] U.S. Cl. .................... 252/117; 252/546; 424/70; 260/404.5
[58] Field of Search .............. 260/404.5 R; 548/352; 252/546, 117; 424/70

[56] References Cited

U.S. PATENT DOCUMENTS

| 3,262,951 | 7/1966 | Katz | 260/404.5 |
| 3,555,041 | 1/1971 | Katz | 548/352 |
| 4,044,034 | 8/1977 | Christiansen | 548/352 |

Primary Examiner—Winston A. Douglas
Assistant Examiner—John F. Niebling
Attorney, Agent, or Firm—Sprung, Felfe, Horn, Lynch & Kramer

[57] ABSTRACT

Disubstituted aliphatic carboxylamidoamines of the general formula:

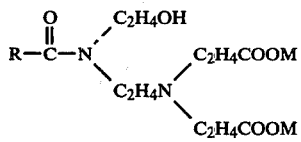

wherein R stands for an aliphatic hydrocarbyl group with 7-17 carbon atoms and M for a hydrogen atom or an alkali metal atom. Detergents and toiletry compositions incorporated with the disubstituted aliphatic carboxylamidoamines are extremely low in irritating property to skin, eyes and mucous membranes.

15 Claims, 5 Drawing Figures

WAVE NUMBER (cm$^{-1}$)

(Ethyl acrylate/Imidazoline derivative)

DISUBSTITUTED ALIPHATIC CARBOXYLAMIDOAMINES AS WELL AS DETERGENTS AND TOILETRY COMPOSITIONS CONTAINING SAME

BACKGROUND OF THE INVENTION

The present invention relates to new compounds useful as amphoteric surface active agents, a process for producing same and the use of the compounds. More particularly, the present invention relates to new disubstituted aliphatic carboxylamidoamines of the general formula:

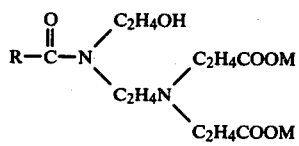

wherein R stands for an aliphatic hydrocarbyl group with 7–7 carbon atoms and M for a hydrogen atom or an alkali metal atom, a process for the production of same and detergents and toiletry composition containing the compounds of the general formula (I) as active ingredients.

Hitherto, compounds of the general formula:

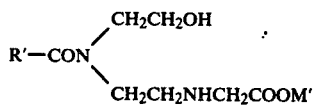

wherein R' stands for a long chain aliphatic hydrocarbyl group and M' for a hydrogen atom or an alkali metal atom, which are obtained by reacting a straight chain aliphatic carboxylic acid ester with aminoethylethanolamine were known as amphoteric surface active agents of substituted amidoamine type (U.S. Pat. Nos. 3,262,951 and 3,941,817).

Such amphoteric surface active agents are employed as detergents, fiber-treating agents, anti-static agents, toiletry bases and the like. In the case of using surface active agents as bases for shampoo, rinse, liquid facial soap and the like toiletries, such surface active agents are required to have no or little irritating property to skin, eyes and mucous membranes. However, the amphoteric surface active agents of substituted amidoamine type represented by the general formula (II) are not satisfactory in this respect and are thus unsuited for the purpose of bases for toiletries.

As a result of extensive researches made for developing amphoteric surface active agents which are less irritative to skin, eyes and mucous memburanes and thus suitable as bases for toiletries, it has now been found that new compounds of the above general formula (I) are suitable for this purpose and that the new compounds of the general formula (I) can be prepared efficiently by saponifying a reaction product of a 1-hydroxyethyl-2-substituted imidazoline, an alkyl acrylate and water with an alkali hydroxide. The present invention has been accomplished on the basis of the above findings.

BRIEF SUMMARY OF THE INVENTION

In accordance with the present invention, therefore, there are provided new disubstituted aliphatic carboxylamidoamines of the general formula (I), a process for the production of the compounds of the general formula (I) characterized by reacting imidazoline derivatives of the general formula:

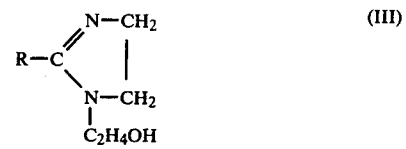

wherein R has the same meaning as given above, with an alkyl acrylate and water and thereafter saponifying the reaction product with an alkali hydroxide, and detergents and toiletry compositions containing the compounds of the general formula (I) as active ingredients.

Accordingly, it is an object of the present invention to provide new surface active agents which are less irritative to skin, eyes and mucous membranes.

It is another object of the present invention to provide a process for the production of the new surface active agents.

It is still another object of the present invention to provide detergents which are less irritative to skin, eyes and mucous membranes.

It is further object of the present invention to provide toiletries which are less irritative to skin, eyes and mucous membranes.

Other objects, features and advantages of the present invention will be apparent from the following description taken in connection with the accompanying drawings wherein.

DETAILED DESCRIPTION OF THE INVENTION

Figure 1:
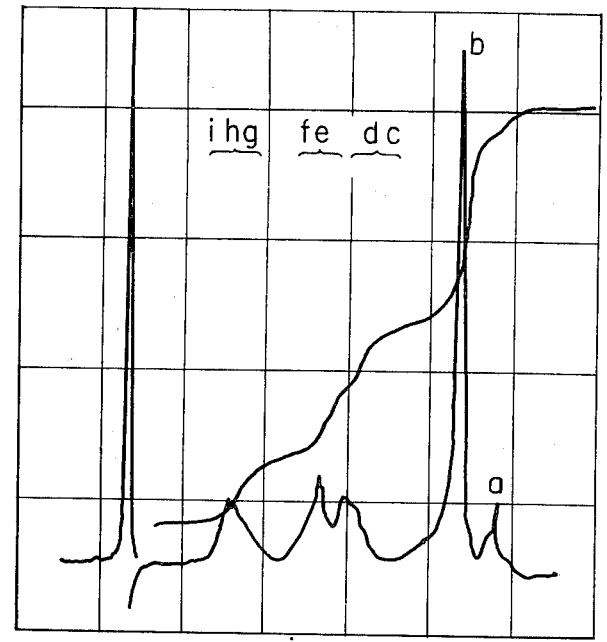
FIG. 1 is an NMR-absorption spectrograph of the compound of this invention.
Figure 1:
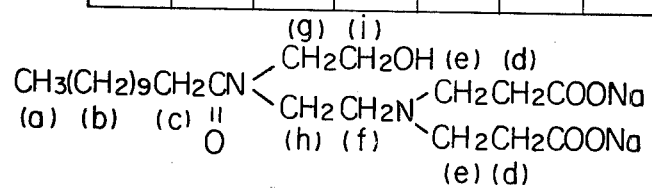

Illustrative of the compounds of the present invention represented by the general formula (I) are N-(2-hydroxyethyl)-N-[di-(2-carboxyethyl) aminoethyl] octanoylamide, N-(2-hydroxyethyl)-N-[di-(2-carboxyethyl) aminoethyl] decanoylamide, N-(2-hydroxyethyl)-N-[di-(2-carboxyethyl) aminoethyl] undecanoylamide, N-(2-hydroxyethyl)-N-[di-(2-carboxyethyl) aminoethyl] dodecanoylamide, N-(2-hydroxyethyl)-N-[di-(2-carboxyethyl) aminoethyl] stearoylamide, N-(2-hydroxyethyl)-N-[di-(2-carboxyethyl) aminoethyl] lauroylamide, N-(2-hydroxyethyl)-N-[di-(2-carboxyethyl) aminoethyl] coconut oil fatty acid amides and sodium and potassium salts thereof.

According to the present invention, the compounds of the above general formula (I) can be prepared by reacting an imidazoline derivative of the general formula:

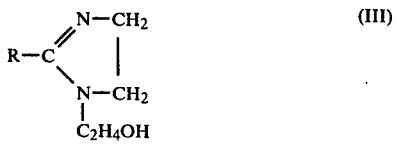

wherein R has the same meaning as given above, with an alkyl acrylate and water and thereafter saponifying the reaction product with an alkali hydroxide.

Examples of the imidazoline derivative of the above general formula (III) include 1-(2-hydroxyethyl)-imidazolines substituted in 2-position thereof by an alkyl group such as octyl, nonyl, decyl, undecyl, dodecyl, pentadecyl, hexadecyl or heptadecyl group or by an alkenyl group such as octenyl, decenyl or pentadecenyl group.

Preferable examples of the alkyl acrylate to be reacted with the imidazoline derivative include methyl acrylate, ethyl acrylate and the like lower alkyl acrylates. This alkyl acrylate is used in an amount of 1.3-2.0 mols per mole of the imidazoline derivative. If the amount of the alkyl acrylate exceeds 2.0 mols, a large amount of unreacted acrylic acid as alkali salt will be present in the product. On the other hand, if the amount is less than 1.3 mols, the amount of unreacted amine will become larger, thus resulting in reduction in the yield of the product.

The amount of water supplied together with the alkyl acrylate to the reaction system is at least 1 mol, preferably within the range of 2.0-3.0 per mole of the imidazoline derivative. If the amount of water is less than 1 mol, the amount of unreacted amine will be increased, thus resulting in reduction in the yield of the product.

The reaction of the imidazoline derivative with the alkyl acrylate and water is carried out at a temperature within the range from room temperature to 100° C., preferably within the range of 60°-80° C. The time required for the reaction is usually within the range from 30 minutes to 4 hours. In the majority of cases, a conversion rate as high as about 99% can be obtained by the reaction carried out for 60 minutes. The reaction may be conducted, if desired, in the presence of an alkaline catalyst but the use of such alkaline catalyst is not especially necessary.

The addition product thus obtained is subjected, without being isolated, to the subsequent saponification treatment with an alkali hydroxide. This saponification treatment is carried out by adding to the reaction product an alkali hydroxide in an almost equimolar amount to the alkyl acrylate and heating the mixture at 50°-100° C. The time required for such saponification is usually about 2 hours at 70° C.

The reaction product thus obtained is distilled under reduced pressure to remove low molecular components contained therein whereby the end product or a reaction product composed predominantly of the end product is retained as a white solid. The end product obtained in this manner as white solid is subjected to a thin layer chromatography whereby a spot is detected to confirm that the product is pure. Results of IR-absorption spectral analysis, NMR-absorption spectral analysis and elementary analysis show that the end product has the structure of the above general formula (1).

The compounds of the present invention are characterized by their extremely low irritating property to skin, eyes and mucous membranes, as compared with the prior art surface active agents of a similar structure.

The compounds of the present invention are useful as detergent, fiber-treating agent, antistatic agent and the like, especially as bases for toiletries, for example, shampoo, hair rinse and liquid facial soap. In the case of using the compounds of the present invention for manufacturing toiletries, the compounds are incorporated with various conventional additives and other optional surface active agents to a desired toiletry composition.

The proportion of the compound of the present invention in such compositions is determined according to the intended use of the composition. Usually, however, the compound of the present invention is added in amount of 0.1-30% by weight based on the composition. In particular, the compound is used preferably in an amount of 0.5-25% by weight in the case of manufacturing detergents and preferably in an amount of 1-20% by weight in the case of manufacturing toiletry compositions.

To further illustrate this invention and not by way of limitation, the following examples are given.

EXAMPLE 1

In a 2 liter 4-necked flask equipped with a stirrer, a condenser and a thermometer were placed 268 g (1.0 mol) of 1-hydroxyethyl-2-undecylimidazoline and 200 g (2.0 mols) of ethyl acrylate. The mixture was stirred for 30 minutes at 25°-35° C. and 36 g (2.0 mols) of water was added thereto whereby the temperature was elevated up to 70° C. The mixture was reacted at this temperature for 2 hours and, after addition of 400 ml of ethyl alcohol and 80 g (2.0 mols) of sodium hydroxide, the mixture was reacted continuously at 70° C. for 3 hours to effect saponification. After completion of the reaction, the reaction mixture was distilled under reduced pressure to remove the ethyl alcohol whereby 473 g of disodium salt of N-(2-hydroxyethyl)-N-[di-(2-carboxyethyl) aminoethyl] lauroylamide was obtained. As a result of a thin layer chromatography where the product showed one spot, it was confirmed that this product was a single substance. As a result of an analysis for determination of carbon and hydrogen, the contents of carbon and hydrogen in this product were 55.62% (55.67% in calc. value) and 8.39% (8.50% in calc. value), respectively. The nitrogen content of this compound was determined as 5.78% (5.90% in calc. value) in a nitrogen analysis according to Kjeldahl method.

Figure 2:
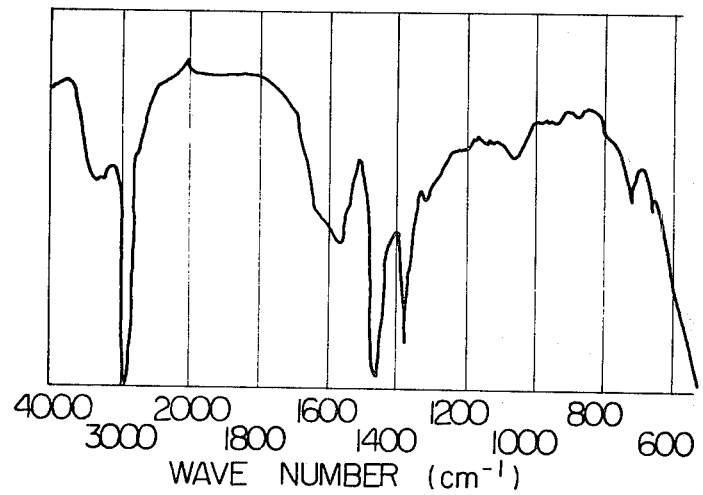
FIGS. 2 and 3 are IR-absorption spectrographs of the compounds of this invention.
Figure 3:
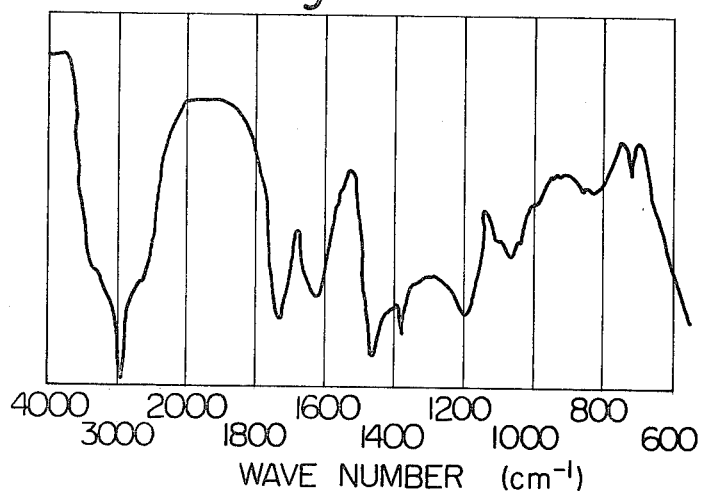

An NMR-absorption spectrum (60 MHz, $D_2O$) and an IR-absorption spectrum (Nujol method) of this compound are shown in FIGS. 1 and 2, respectively. An IR-absorption spectrum of a product obtained by neutralizing this compound with hydrochloric acid is also shown in FIG. 3.

EXAMPLE 2

In the same flask as described in Example 1 were placed 268 g (1.0 mol) of 1-hydroxyethyl-2-alkylimidazoline manufactured from coconut oil fatty acids (average molecular weight: 200; AV 280) and 200 g (2.0 mols) of ethyl acrylate. The mixture was stirred for 30 minutes at 25°-30° C. and 36 g (2.0 mols) of water was then added thereto whereby the temperature of the mixture was elevated up to 70° C. The mixture was reacted for 2 hours at this temperature and 539 g of water was then added thereto. Further, 160 g (2.0 mols) of a 50% aqueous solution of sodium hydroxide was added and the mixture was heated at 70° C. for 2 hours to effect saponification. The reaction mixture was then distilled under reduced pressure to obtain 39.4% of an evaporation residue. In this manner, disodium salt of N-(2-hydroxyethyl)-N-[di-(2-carboxyethyl) aminoethyl] coconut oil fatty acid amide was obtained, which showed a pH value of 12.6. This product contained 0.2% by weight of unreacted amine and 0.1% by weight of sodium acrylate.

EXAMPLE 3

Except that the amount of ethyl acrylate was 150 g (1.5 mols), the amount of water added during the saponification reaction was 494 g and the amount of a 50% aqueous solution of sodium hydroxide was 120 g (1.5 mols), the experiment of Example 2 was repeated under the same conditions whereby a reaction product showing a pH value of 12.9 was obtained as 40% by weight of an evaporation residue. This product was a mixture of 60% by weight of disodium salt of N-(2-hydroxyethyl)-N-[di-(2-carboxyethyl) aminoethyl] coconut oil fatty acid amide and 40% by weight of sodium salt of N-(2-hydroxyethyl)-N-(2-carboxyethylaminoethyl) coconut oil fatty acid amide and contained 0.3% by weight of each of unreacted amine and sodium acrylate.

EXAMPLE 4

Except that 352 g (1.0 mol) of 1-hydroxyethyl-2-heptadecylimidazoline was used as the starting imidazoline derivative, the treatments were carried out in the same manner as described in Example 2 whereby an aqueous solution of disodium salt of N-(2-hydroxyethyl)-N-[di-(2-carboxyethyl) aminoethyl] stearylamide was obtained. This solution showed a pH value of 12.5 and gave 43.3% by weight of an evaporation residue which contained as impurities 0.2% by weight of unreacted amine and 0.1% by weight of sodium acrylate.

EXAMPLE 5

Except that 268 g (1.0 mol) of 1-hydroxyethyl-2-undecylimidazoline and 172 g (2.0 mols) of methyl acrylate were used, the experiment of Example 2 was repeated under the same conditions whereby disodium salt of N-(2-hydroxyethyl)-N-[di-(2-carboxyethyl) aminoethyl] undecanecarboxylamide was obtained. This product showed a pH value of 12.5 and the evaporation residue was 40.3% by weight which contained 0.2% by weight of unreacted amine and 0.1% by weight of sodium acrylate.

REFERENTIAL EXAMPLE 1

In accordance with the procedure disclosed in U.S. Pat. No. 3,941,817, 214 g (1.0 mol) of coconut oil fatty acid methyl ester obtained from a coconut oil fatty acid having an average molecular weight of 200, 107 g (1.03 mols) of aminoethylethanolamine and a 25% sodium methoxide solution in methyl alcohol were placed in a 1 l 4-necked flask equipped with a stirrer, a thermometer, a nitrogen gas inlet and a condenser connected to a vacuum pump. The mixture was gradually heated under a reduced pressure of 150 mmHg while introducing nitrogen thereinto. At a temperature of 100°-150° C., 31 g of the methyl alcohol was recovered whereby 286 g of N-coconut oil acrylated-N-hydroxyethylethylenediamine as obtained as residue.

The nitrogen inlet was then replaced by a dropping funnel and 375 g of water and 94.5 g (1.0 mol) of monochloroacetic acid were successively added and the mixture was cooled to 45° C. To this mixture was added carefully over a period of 10 minutes 160 g (2.0 mols) of an aqueous solution of 50% by weight of sodium hydroxide lest the external temperature should exceed 55° C. After addition of the solution, the mixture was reacted for 3 hours at 50°-60° C. and then for 2 hours at 80°-90° C. Sodium salt of N-(2-hydroxyethyl)-N-(2-carboxymethyl) aminoethyl coconut oil fatty acid amide was thus obtained.

REFERENTIAL EXAMPLE 2

The compound (Sample A) obtained in Example 1, the compound (Sample B) obtained in Example 3 and the compound (Sample C) obtained in Referential Example 1 were respectively dissolved in water to prepare a 8 wt% aqueous solution of each sample. A group consisting of three white male rabbits was treated with 0.1 ml of the aqueous solution and an eye-irritation test was performed according to Draize method. A result of the test is shown in Table 1.

Table 1

| Observation time (hr) | Cornea | | | | Hyperaemia of Iris | | | | Conjunctiva | | | | Total | | | | 24 ∫ 168 |
|---|---|---|---|---|---|---|---|---|---|---|---|---|---|---|---|---|---|
| | 24 | 48 | 72 | 168 | 24 | 48 | 72 | 168 | 24 | 48 | 72 | 168 | 24 | 48 | 72 | 168 | |
| Sample A | 0 | 0 | 0 | 0 | 0 | 0 | 0 | 0 | 5 | 3 | 2 | 1 | 5 | 3 | 2 | 1 | 11 |
| Sample B | 2 | 2 | 0 | 0 | 0 | 0 | 0 | 0 | 8 | 4 | 1 | 0 | 10 | 6 | 1 | 0 | 17 |
| Sample C | 13 | 15 | 18 | 13 | 3 | 3 | 5 | 2 | 11 | 9 | 7 | 3 | 27 | 29 | 30 | 18 | 92 |

In the case of Sample A, i.e. the compound of the present invention, no trouble occurred in cornea and hyperaemia of iris was not found. Only a slight edema of conjunctiva was observed but it was not so serious. Thus, the compound of the present invention was found to be extremely low in eye-irritation.

EXAMPLE 6

Figure 4:
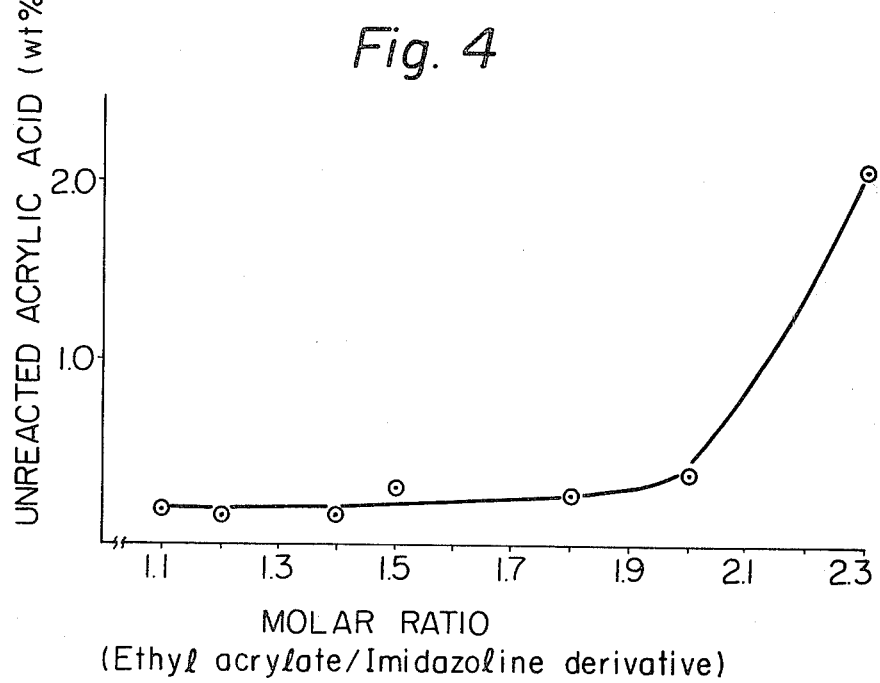
FIGS. 4 and 5 are graphs showing the relation between the molar ratio of the starting material and the quantity of impurities in the product in the process of the present invention.
Figure 5:
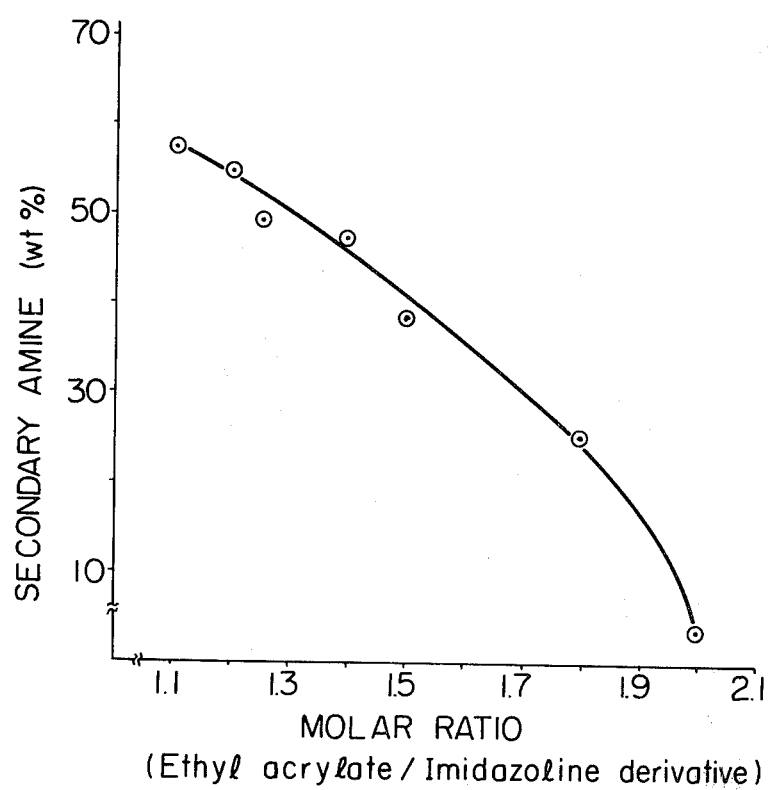

Except that the molar ratio of ethyl acrylate to 1-hydroxyethyl-2-undecylimidazoline was varied, the reaction was carried out under the same conditions as described in Example 1 to prepare disodium salt of N-(2-hydroxyethyl)-N-[di-(2-carboxyethyl) aminoethyl] lauroylamide. FIG. 4 is a graph showing the relation between the molar ratio and the amount of acrylic acid (sodium acrylate) formed by hydrolysis of unreacted ethyl acrylate in the above reaction. FIG. 5 is a graph showing the relation between the molar ratio and the amount of a secondary amine formed as by-product.

As is evident from these graphs, the molar ratio of an alkyl acrylate to the imidazoline derivative is preferably within the range from 1.3 to 2.0.

The following examples illustrate detergents and toiletry compositions in which the compounds of the present invention are used.

EXAMPLE 7

Using disodium salt of N-(2-hydroxyethyl)-N-[di-(2-carboxyethyl) aminoethyl] coconut oil fatty acid amide as a typical compound of the present invention, a low irritative shampoo was manufactured according to the following recipe:

| Ingredients | % by weight |
| --- | --- |
| The compound of the present invention | 15 |
| Coconut oil fatty acid diethanolamide | 3 |
| Citric acid monohydrate | 2 |
| Ethyl p-hydroxybenzoate | 0,5 |
| Preservative, perfume and colorant | Adequate amount |
| Deionized water | Balance |

EXAMPLE 8

Using the same compound as described in Example 7, a hair rinse of emulsion type was prepared according to the following recipe:

| Ingredients | % by weight |
| --- | --- |
| The compound of the present invention | 2 |
| Distearyldimethylammonium chloride | 3 |
| Ethyleneglycol monostearate | 1 |
| Polyoxyethyleneoleyl alcohol | 1 |
| Glycerol | 5 |
| Perfume and colorant | Adequate amount |
| Deionized water | Balance |

This hair rinse was substantially less irritative to eyes and was effective for facilitating the use of a comb for rinsed hair.

EXAMPLE 9

Using the same compound as described in Example 7, a liquid facial soap was manufactured according to the following recipe:

| Ingredients | % by weight |
| --- | --- |
| The compound of the present invention | 18 |
| Lauroyldiethanolamide | 5 |
| citric acid monohydrate | 1 |
| Perfume and colorant | Adequate amount |
| Deionized water | Balance |

This soap showed no irritation to eyes.

EXAMPLE 10

Using the same compound as described in Example 7, a liquid detergent for domestic use was manufactured according to the following recipe:

| Ingredients | % by weight |
| --- | --- |
| The compound of the present invention | 9 |
| Lauroyldiethanolamide | 3 |
| Sodium lauryl ether sulfate | 10 |
| Sodium chloride | 1 |
| Citric acid monochloride | 1 |
| Perfume and colorant | Adequate amount |
| Deionized water | Balance |

This detergent was equivalent in detergency to the prior art one but was superior in low irritation to the prior art oen.

What is claimed is:

1. A disubstituted aliphatic carboxylamidoamine of the general formula:

$$R-\overset{O}{\underset{\|}{C}}-N\diagdown\begin{array}{l}C_2H_4OH\\ C_2H_4N\diagup\begin{array}{l}C_2H_4COOM\\ C_2H_4COOM\end{array}\end{array}$$

wherein R stands for an aliphatic hydrocarbyl group with 7–17 carbon atoms and M for a hydrogen atom or an alkali metal atom.

2. A disubstituted aliphatic carboxylamidoamine according to claim 1 wherein M in the general formula stands for sodium.

3. A disubstituted aliphatic carboxylamidoamine according to claim 1 wherein M in the general formula stands for potassium.

4. A disubstituted aliphatic carboxylamidoamine according to claim 1 wherein R in the general formula stands for an alkyl group with 7–17 carbon atoms.

5. A disubstituted aliphatic carboxylamidoamine according to claim 1 wherein R in the general formula stands for an alkenyl group with 7–17 carbon atoms.

6. A disubstituted aliphatic carboxylamidoamine according to claim 1 wherein the acyl group $$R-\overset{O}{\underset{\|}{C}}-$$

in the general formula is lauroyl group, stearoyl group or an acyl group derived from coconut oil fatty acids.

7. A process for the production of disubstituted aliphatic carboxylamidoamines of the general formula:

$$R-\overset{O}{\underset{\|}{C}}-N\diagdown\begin{array}{l}C_2H_4OH\\ C_2H_4N\diagup\begin{array}{l}C_2H_4COOM\\ C_2H_4COOM\end{array}\end{array}$$

wherein R stands for an aliphatic hydrocarbyl group with 7–17 carbon atoms and M for a hydrogen atom or an alkali metal atom, characterized by reacting an imidazoline derivative of the general formula:

$$R-C\diagup\begin{array}{l}N-CH_2\\ \diagdown N-CH_2\\ \phantom{xxx}|\\ \phantom{xxx}C_2H_4OH\end{array}\quad\text{(III)}$$

wherein R has the same meaning as given above, with an alkyl acrylate and water and thereafter saponifying the reaction product with an alkali hydroxide.

8. A process according to claim 7 wherein 1.3–2.0 mols of said alkyl acrylate and at least 1.0 mol of water are used per mol of said imidazoline derivative.

9. A process according to claim 7 wherein said alkyl acrylate is methyl or ethyl acrylate.

10. A detergent which comprises as active ingredient a disubstituted aliphatic carboxylamidoamine of the general formula:

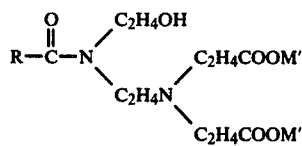

wherein R stands for an aliphatic hydrocarbyl group with 7–17 carbon atoms and M′ for an alkali metal atom.

11. A detergent according to claim 10 wherein M′ in the general formula is sodium.

12. A detergent according to claim 10 wherein said disubstituted aliphatic carboxylamidoamine of the general formula is contained in an amount of 0.1–30% by weight.

13. A toiletry composition which comprises as active ingredient a dialkali metal salt of a disubstituted aliphatic carboxylamidoamine of the general formula:

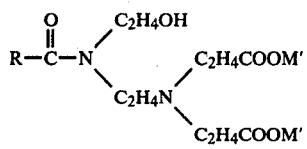

wherein R stands for an aliphatic hydrocarbyl group with 7–17 carbon atoms and M′ for an alkali metal atom.

14. A toiletry composition according to claim 13 wherein M′ in the general formula is sodium.

15. A toiletry composition according to claim 13 wherein said disubstituted aliphatic carboxylamidoamine of the general formula is contained in an amount of 0.1–30% by weight.

* * * * *